United States Patent [19]

Watts

[11] 4,267,175
[45] May 12, 1981

[54] BENZAMIDE DERIVATIVES

[75] Inventor: Eric A. Watts, Harlow, England

[73] Assignee: Beecham Group Limited, England

[21] Appl. No.: 18,625

[22] Filed: Mar. 8, 1979

Related U.S. Application Data

[63] Continuation-in-part of Ser. No. 799,308, May 19, 1977, abandoned.

[30] Foreign Application Priority Data

Jun. 3, 1976 [GB] United Kingdom ............... 22879/76
Jan. 1, 1977 [GB] United Kingdom ................. 3474/77

[51] Int. Cl.$^3$ .................... A61K 31/495; C07D 295/00
[52] U.S. Cl. ..................................... 424/244; 424/250; 260/239 BC; 544/374; 544/382
[58] Field of Search ................ 544/382; 424/250, 244; 260/239 BC

[56] References Cited

U.S. PATENT DOCUMENTS 3,177,252  4/1965  Thominet ......................... 260/559 S Primary Examiner—Donald G. Daus
Assistant Examiner—James H. Turnipseed
Attorney, Agent, or Firm—Jacobs & Jacobs

[57] ABSTRACT

A compound of the formula (I), and pharmaceutically acceptable salts thereof:

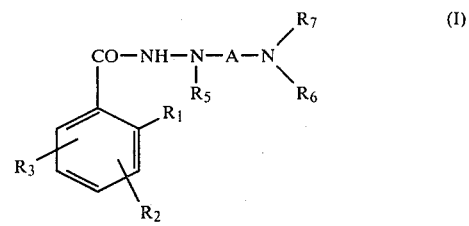

wherein:
$R_1$ is a $C_{1-6}$ alkoxy group;
$R_2$ and $R_3$ are the same or different and are hydrogen, halogen, $CF_3$, hydroxy, $C_{1-6}$ alkoxy, $C_{2-7}$ acyl, amino, amino substituted by one or two $C_{1-6}$ alkyl groups, $C_{2-10}$ acyl amino, aminosulphone, aminosulphone substituted by one or two $C_{1-6}$ alkyl groups, $C_{1-6}$ alkyl sulphone or nitro groups; and
A is a $C_{2-4}$ alkylene group;
$R_5$ and $R_6$ are joined so that they form with the —N—A—N— group to which they are attached, a 6, 7 or 8 membered heterocyclic ring;
$R_7$ is a $C_{1-6}$ alkyl group, or an aryl —$C_{1-6}$ akyl group in which the alkyl moiety is optionally substituted by a $C_{1-6}$ alkyl or aryl group; have useful pharmacological activity, such as the ability to regulate the gastrointestinal function and to treat emesis.

37 Claims, No Drawings

BENZAMIDE DERIVATIVES

CROSS-REFERENCE TO RELATED APPLICATION

This is a continuation-in-part of U.S. Ser. No. 799,308 filed May 19, 1977, now abandoned.

BACKGROUND OF THE INVENTION (1) Field of the Invention

This invention relates to novel substituted benzamides having useful pharmacological properties, to pharmaceutical compositions containing them, and to a method for their use.

(2) Description of the Prior Art

U.S. Pat. No. 3,177,252 describes inter alia the preparation and properties of the compound N-(2-diethyl aminoethyl)-2-methoxy-4-amino-5-chlorobenzamide. This compound, which is known by the generic name metoclopramide, has become well established in medical therapy for its useful pharmacological properties, which include activity against emesis and ability to regulate the gastrointestinal function.

DETAILED DESCRIPTION

It is one object of this invention to provide a novel class of substituted benzamides which also has useful pharmacological activity.

This object has been achieved by the provision of a compound of the formula (I), and pharmaceutically acceptable salts thereof:

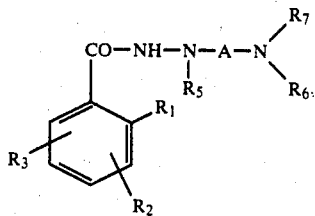

wherein:

$R_1$ is a $C_{1-6}$ alkoxy group;

$R_2$ and $R_3$ are the same or different and are hydrogen, halogen, $CF_3$, hydroxy, $C_{1-6}$ alkoxy, $C_{2-7}$ acyl, amino, amino substituted by one or two $C_{1-6}$ alkyl groups, $C_{2-10}$ acyl amino, aminosulphone, aminosulphone substituted by one or two $C_{1-6}$ alkyl groups, $C_{1-6}$ alkylsulphone or nitro groups; and A is a $C_{2-4}$ alkylene group;

$R_5$ and $R_6$ are joined so that they form, with the —N—A—N— group to which they are attached, a 6, 7 or 8 membered heterocyclic ring;

$R_7$ is a $C_{1-6}$ alkyl group, or an aryl-$C_{1-6}$ alkyl group in which the alkyl moiety is optionally substituted by a $C_{1-6}$ alkyl or aryl group.

Suitable examples of the group $R_1$ include methoxy, ethoxy and n- and iso-propoxy. Preferably $R_1$ is a methoxy group.

Suitable examples of the groups $R_2$ and $R_3$ include the following groups: hydrogen, chlorine, bromine, $CF_3$, hydroxy methoxy, ethoxy, n- and iso-propoxy, n- and sec- and tert-butoxy, acetyl, propionyl, butyryl, amino, amino substituted by one or two methyl, ethyl, n- or iso-propyl, n-, sec- or tert-butyl groups, $C_{2-7}$ acylamino such as acetylamino, propionylamino, butyramino; aminosulphone, aminosulphone substituted by one or two methyl, ethyl, n- or iso-propyl, n- sec- or tert-butyl groups, and methyl, ethyl and n- and iso-propylsulphone, and nitro.

More suitably $R_2$ is a group $NHCYR^1_2$ wherein Y is oxygen or sulphur (preferably oxygen), $R^1_2$ is hydrogen, $C_{1-6}$ alkyl, $C_{1-6}$ alkyl substituted by one, two or three halogen atoms (preferably by one, two or three chlorine atoms, or by three fluorine atoms at the same carbon atom), or a group $—(CH_2)_r—NR_aR_b$ wherein r is 0 to 3, $R_a$ and $R_b$ are hydrogen, $C_{1-6}$ alkyl or together with the nitrogen atom form a 5, 6 or 7 membered heterocyclic ring which may contain one other hetero atom (suitably oxygen). Examples of such groups $R_2$ include $NHCOCH_2Cl$. $R_2$ may also be a group $NHCY.O.R^1_2$, wherein Y and $R^1_2$ are as defined. In this case Y is preferably oxygen, r is suitably 2 or 3, and preferably $R^1_2$ is $C_{1-6}$ alkyl.

Particularly suitable $R_2$ and $R_3$ groups include hydrogen, halogen, amino and substituted amino as defined.

It is generally preferred that $R_2$ is in the 4-position relative to the carbonyl side chain for greater activity in the resultant compound of the formula (I). For the same reason it is generally preferred that $R_3$ is in the 5-position relative to the carbonyl side chain.

Particularly preferred $R_2$ groups include 4-amino and 4-(substituted amino) as defined. Preferably $R_2$ is 4-amino. Particularly preferred $R_3$ groups include 5-halo, such as 5-chloro.

When A is a $C_{2-4}$ alkylene group, it is suitably ethylene or n-propylene, preferably ethylene.

When $R_5$ is hydrogen or a $C_{1-6}$ alkyl group, it is suitably hydrogen, methyl, ethyl or n- or iso-propyl. More suitably $R_5$ is methyl.

When $R_7$ is a $C_{1-6}$ alkyl group, or optionally substituted aryl-$C_{1-6}$ alkyl group as defined, suitable examples of such groups include methyl, ethyl, n- and iso-propyl and n-butyl; and aryl-methyl, ethyl, and n- and iso-propyl groups optionally substituted in the alkyl moiety by a methyl, ethyl or aryl group. When used herein aryl is limited to monocyclic aryl. Suitable examples of such aryl groups include phenyl, thienyl, pyridyl, and pyrimidyl groups optionally substituted by hydrogen, halogen, $C_{1-6}$ alkyl, $C_{1-6}$ alkoxy, hydroxy, nitro, amino, amino substituted by one or two $C_{1-6}$ alkyl groups, or $CF_3$. Most suitably aryl represents an optionally substituted phenyl group. Preferred groups $R_7$ include $C_{1-6}$ alkyl groups such as methyl; and aryl-$C_{1-6}$ alkyl groups such as benzyl.

$R_5$ and $R_6$ may be joined as defined above, to form a 6, 7 or 8, preferably 6, membered heterocyclic ring. In this case the carbonyl side chain of the benzene nucleus in the compound of the formula (I) may suitably be of formula (II):

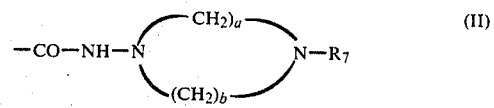

wherein a and b are each 2 or 3 and $R_7$ is as defined in formula (I).

Preferably a=b=2 in formula (II). Preferably $R_7$ is $C_{1-6}$ alkyl, such as methyl or butyl; or benzyl; most preferably methyl.

From the aforesaid it will be realised that certain particularly suitable compounds of the formula (I) will be of the following formula:

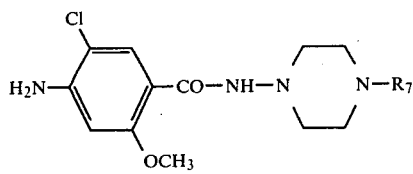

(VII)

In formula (VII), R₇ is suitably $C_{1-6}$ alkyl, such as methyl or ethyl; or benzyl.

Other suitable compounds are of formula (VII) as defined but wherein the 4-amino is substituted as hereinbefore defined.

A preferred class of compounds are those of formula (VII), optionally substituted as defined at the 4-amino group.

The pharmaceutically acceptable salts of the compounds of the formula (I) include acid addition salts with conventional acids such as hydrochloric, hydrobromic, phosphoric, sulphuric, citric, tartaric, lactic and acetic acid and the like.

The pharmaceutically acceptable salts of the compounds of the formula (I) also include quaternary ammonium salts. Examples of such salts include salts with compounds such as $R_8$-X wherein $R_8$ is $C_{1-6}$ alkyl, phenyl-$C_{1-6}$ alkyl or $C_{5-7}$ cycloalkyl, and X is an anion of an acid. Suitable examples of $R_8$ include methyl, ethyl and n- and iso-propyl; and benzyl and phenyl ethyl. Suitable examples of X include the halides such as chloride, bromie and iodide.

The invention also provides a process for the preparation of a compound of the formula (I), which process comprises reacting an acid of formula (IX), or a reactive derivative thereof:

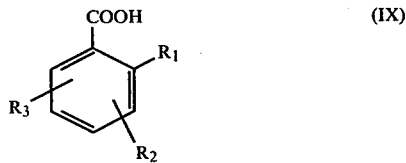

(IX)

wherein $R_1$, $R_2$ and $R_3$ are as defined in formula (I) with a compound of formula (X): $H_2N—N(R_5)—ANR_6R_7$, wherein A, $R_5$, $R_6$ and $R_7$ are as defined in formula (I), and thereafter if desired or necessary converting a group $R_2$ or $R_3$ in the thus formed compound of the formula (I) to another group $R_2$ or $R_3$.

The acid addition salts of compounds of the formula (I) may be prepared in entirely conventional manner by reacting the thus formed compound of the formula (I) in base form with the chosen acid.

The quaternary ammonium salts of the compounds of the formula (I) may be prepared in conventional manner for such salts, such as by reaction of the chosen compound of the formula (I) with a compound $R_8X$ as defined. This reaction is suitably carried out in an appropriate solvent such as acetone, methanol, ethanol and the like, at ambient or raised temperature and pressure.

'Reactive derivative' means a derivative of the compound (IX) which can be reacted with the compound (X) to form an amido linkage between the acid group of the compound (IX) and the —NH₂ amino group of the compound (X).

Often this reactive derivative will be the acid halide, such as the acid chloride, of the acid (IX). In such cases, the reaction will normally be carried out in an inert solvent, preferably in the presence of an acid acceptor. The inert solvent can be any solvent inert to both reactants such as benzene, toluene, diethylether and the like. The acid acceptor is normally an organic base such as a tertiary amine, e.g., triethylamine, trimethylamine, pyridine, picoline. It may also be any inorganic acid acceptor, such as calcium carbonate and sodium carbonate and the like. It should also be noted that it is possible to use certain acid acceptors as the inert solvent as well, for example organic bases.

Another useful reactive derivative of the acid (IX) that may be used is an acid ester, such as methyl, ethyl, propyl or butyl ester, in which case the reaction is normally carried out by heating the reactants together in an inert solvent such as ethylene glycol.

The reaction may also be carried out by forming an anhydride of the acid (IX) in the usual manner, and reacting that with the compound (X)—normally a conventional mixed anhydride will be used; or by reacting the acid (IX) and the compound (X) in the presence of a dehydrating catalyst such as a carbodiimide, for example dicyclohexyl carbodiimide.

The interconversion of suitable groups $R_2$ and $R_3$ after formation of a compound of the formula (I) may be carried out by conventional methods. By way of example, nitro groups may be reduced to amino groups in the normal manner, and acylamino groups may be converted to amino also by conventional methods. Also a compound of the formula (I) wherein $R_2$ or $R_3$ is halogen can be prepared by a conventional halogenation of the corresponding compound of the formula (I) wherein the said $R_2$ or $R_3$ is hydrogen.

Compounds wherein $R_2$ is an amino group can be converted to compounds wherein $R_2$ is a group $NHCYR^1_2$ or $NHCY.O.R^1_2$ as defined by acylation with an acylating derivative of the corresponding acid of formula $HO.YC.R^1_2$ or $HO.YC.OR^1_2$ in known manner. Normally however compounds wherein $R_2$ is a group $NHCYNR_aR_b$ will be prepared by reacting the corresponding compound wherein $R_2$ is amino with an isocyanate or an isothiocyanate. Compounds wherein $R^1_2$ is mono halogenated alkyl may be reacted with amines $H-NR_aR_b$ to give corresponding compounds wherein $R^1_2$ is alkyl-$NR_aR_b$, again in known manner.

The acids of formula (IX) and the compounds $H_2N—N(R_5)—ANR_6R_7$ are either known compounds or can be prepared by analogous processes to known compounds.

The compounds of the formula (I) have useful pharmacological properties. For example they may be used for the treatment of disorders of the gastrointestinal function, such as retarded gastric emptying, dyspepsia, flatulence, oesophageal reflux, peptic ulcer and the like. They may also be of use as anti-emetics. Some of the compounds may also be used as neuro leptics. The invention therefore also provides a pharmaceutical composition comprising a compound of the formula (I) or a pharmaceutically acceptable salt thereof, together with a pharmaceutically acceptable carrier. Such compositions may be adapted for oral or parenteral administration, and as such may be in the form of tablets, capsules, syrups, reconstitutable powders, injectable and infusable solutions or suspensions and the like. The compositions may also be in the form of suppositories and the like. Normally orally administrable compositions are preferred.

The invention further provides a method of treatment of maladies in humans comprising the administration of an effective amount of a compound of the formula (I) or a pharmaceutically acceptable salt thereof. The 'effective amount' will depend in the usual way on a number of factors such as the nature and severity of the malady to be treated, and the actual compound used. Usually we have found that a dose of 0.1 to 50, suitably 1 to 4 mg/kg per day is quite sufficient to achieve a satisfactory treatment.

It has been found that compounds of the formula (I) have the ability to potentiate the effect of conventional analgesics in migraine treatment when administered concurrently with the analgesic. Thus the invention provides a pharmaceutical composition comprising a compound of the formula (I) and an analgesic.

The compound of the formula (I) and the analgesic, such as aspirin or paracetamol, will be present in the composition in amounts generally similar to their usual effective dose.

The composition can be a combination product, for example a tablet or capsule containing both a compound of the formula (I) and an analgesic for oral administration, or a twin pack comprising the two active ingredients made up for separate administration.

The invention accordingly provides a method of treatment of migraine comprising the administration to the sufferer of a compound of the formula (I) and an analgesic.

The invention in its different aspects also of course extends to hydrates of the compounds of the formula (I).

The following Examples illustrate the invention.

EXAMPLE 1

4-Amino-5-chloro-2-methoxy-N-[4-benzyl-1-piperazinyl]benzamide

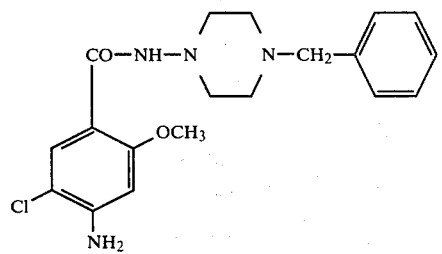

4-Acetylamino-5-chloro-methoxybenzoic acid (3.50 g, 0.144 mole) was treated with thionyl chloride (25 ml) at 50° for ½ hour. The mixture was evaporated in vacuo and the residue azeotroped twice with anhydrous benzene (100 ml) and redissolved in anhydrous benzene (100 ml). Triethylamine (1.45 g) was added followed by 1-amino-4-benzylpiperazine (2.75 g 0.144 mole) and the reaction left for 6 hours at room temperature. The mixture was evaporated in vacuo, taken up in water (50 ml) basified with dilute sodium hydroxide (10%) and extracted with chloroform. Evaporation of the dried (MgSO$_4$) chloroform extract gave 4-acetylamino-5-chloro-2-methoxy-N-[4-benzyl-1-piperazinyl]benzamide (3.50 g; 58%) as colourless microcrystals m.p. 211°-213° C. A sample recrystallised from benzene gave m.p. 212° C.

Treatment of the above with 85% potassium hydroxide (3.0 g) in aqueous ethanol (50 ml) for 6 hours at reflux gave on cooling 4-amino-5-chloro-2-methoxy-N-[4-benzyl-1-piperazinyl]benzamide (1.90 g; 70%) as colourless microcrystals m.p. 185° C. (ex ethylacetate/light petroleum 40°-60°).

A solution in ethanol of the above when treated with ethereal hydrogen chloride gave a hydrochloride salt as colourless crystals m.p. 177°-178° C.

| C$_{19}$H$_{23}$ClN$_4$O$_2$ | Requires: | C = 60.88 | H = 6.14 N = 14.95 |
|---|---|---|---|
| | | Cl = 9.48 | |
| | Found: | C = 61.24 | H = 6.41 N = 15.32 |
| | | Cl = 9.29 | |

EXAMPLE 2

4-Amino-5-chloro-2-methoxy-N-[4-methyl-1-piperazinyl]benzamide

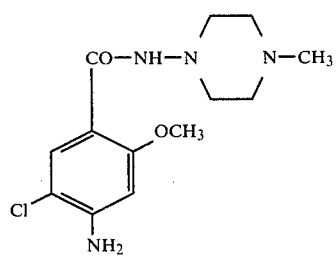

4-acetylamino-5-chloro-2-methoxy benzoyl chloride (2.70 g, 0.0103 mole) in anhydrous benzene (100 ml) in the presence of triethylamine (1.1 g) was treated with 4-methyl-1-amino piperazine (1.18 g). After 6 hours the reaction mixture was basified with dilute sodium hydroxide and extracted with hot ethyl acetate. On cooling the extracts yielded 4-acetylamino-5-chloro-2-methoxy-N-[4-methyl-1-piperazinyl]benzamide (1.72 g), m.p. 198°-200° C.

Without purification the acetylamino compound (1.72 g) was hydrolysed in aqueous alcoholic potassium hydroxide (10 mls) at 80° for 1 hour to give 4-amino-5-chloro-2-methoxy-N-[4-methyl-1-piperazinyl]benzamide (1.67 g, 56%) as the monohydrate, m.p. 159°-150°, (softening at 112° C.).

EXAMPLE 3

4-acetylamino-5-chloro-2-methoxy-N-[4-methyl-1-piperazinyl]benzamide (1.31 g) was dissolved in ethanol and treated with anhydrous ethereal hydrogen chloride to give the monohydrochloride (970 mg), recrystallised from ethanol/anhydrous ether to m.p. 224°-230° C.

EXAMPLE 4

4-amino-5-chloro-2-methoxy-N-[4-methyl-1-piperazinyl]benzamide (700 mg) gives the monohydrochloride hemihydrate (m.p. 237°-239° C.) when treated as in Example 3.

EXAMPLE 5

4-Amino-5-chloro-2-methoxy-N-[4-ethyl-1-piperazinyl]benzamide

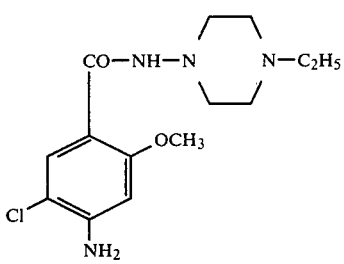

Ethyl iodide (8.13 g, 0.052 mole) was added to acetone (80 ml) containing N-nitroso piperazine (6.0 g, 0.052 mole) (prepared as described in U.S. Pat. No. 2,907,767) and anhydrous potassium carbonate (7.3 g, 0.052 mole). The mixture was heated under reflux for 24 hours, cooled, treated with water (50 ml) evaporated to ½ volume and extracted with ether (3×150 ml). The combined extracts were dried ($K_2CO_3$) filtered and evaporated in vacuo to yield N-ethyl-N'-nitrosopiperazine (7.71 g, 98%), as a straw coloured oil.

A solution of N-ethyl-N'-nitroso piperazine (4.0 g, 0.028 mole) in anhydrous freshly distilled tetrahydrofuran (80 ml) was added dropwise to a stirred suspension of lithium aluminium hydride (1.5 g, excess) under nitrogen in anhydrous tetahydrofuran (160 ml) at 20°–25° C. After addition stirring was continued for a further 8 hours. Work up via controlled addition of water (1.5 ml), 10% sodium hydroxide (2.25 ml) and water (3.75 ml) gave N-amino-N'-ethyl piperazine (2.26 g, 63%) as a pale straw coloured oil.

Subsequent treatment with 4-acetylamino-5-chloro-2-methoxy benzoic acid (4.27 g, 0.0175 mole) as the acid chloride in anhydrous benzene (100 ml) containing tri-ethylamine (2.0 g) gave 4-acetylamino-5-chloro-2-methoxy-N-[4-ethyl-1-piperazinyl]benzamide (4.16 g, 67%) as a foam (ex. ethyl acetate).

Hydrolysis in aqueous alcoholic potassium hydroxide (1.5 g in ethanol (10 ml) containing water (4 ml)) at 80° C. for 1 hour gave 4-amino-5-chloro-2-methoxy-N-[4-ethyl-1-piperazinyl]benzamide (2.3 g, 65%) as colourless microcrystals, m.p. 177°–178.5° C. (ex. EtOAc).

EXAMPLE 6

4-Amino-5-chloro-2-methoxy-N-[4-n-butyl-1-piperazinyl]benzamide

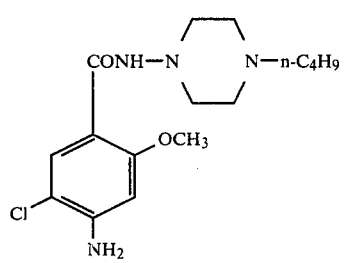

Reaction between 4-acetylamino-5-chloro-2-methoxy benzoic acid (3.2 g, 0.013 mole), triethylamine (1.3 g) and N-n-butyl-N'-amino piperazine (2.06 g) (prepared in similar manner to that described in Example 5) and hydrolysis as described in Example 1 gave 4-amino-5-chloro-2-methoxy-N-[4-n-butyl-1-piperazinyl]benzamide (2.80 g, 63%) as colourless microcrystals, m.p. 173.5°–174° C. (ex. EtOAc/light petrol 40°–60°).

EXAMPLE 7

4-Amino-5-chloro-2-methoxy-N-{[4-(4-chlorobenzyl)]1-piperazinyl}benzamide

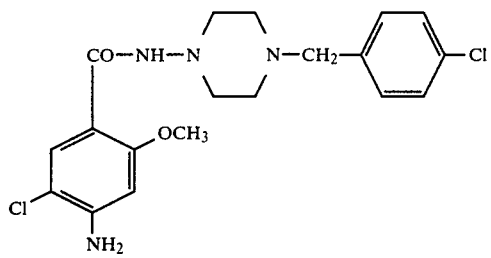

Reaction between 4-acetylamino-5-chloro-2-methoxy benzoic acid (3,0 g, 0.0123 mole), triethylamine (1.3 g) and N-amino-N'-4-chloro benzyl piperazine (2.8 g) and hydrolysis as described in Example 1 gave 4-amino-5-chloro-2-methoxy-N-{[4-(4-chloro benzyl)]-1-piperazinyl benzamide} (1.96 g, 44%) as colourless microcrystals, m.p. 196°–197° C. (ex. EtOAc/light petrol 40°–60°).

EXAMPLE 8

4-Amino-5-chloro-2-methoxy-N-[4-(4-methoxybenzyl)-1-piperazinyl]benzamide

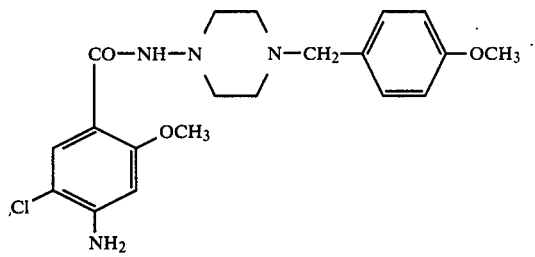

Reaction between 4-acetylamino-5-chloro-2-methoxy benzoic acid (3.0 g, 0.012 mole), tri-ethylamine (1.3 g) and N-amino-N-(4-methoxy benzyl) piperazine (2.72 g, 0.012 mole) and hydrolysis as described in Example 1 gave 4-amino-5-chloro-2-methoxy-N-[4-(4-methoxybenzyl)-1-piperazinyl]benzamide (3.93 g, 81%) as colourless microcrystals, m.p. 154°–156° C. (ex. EtOAc).

EXAMPLE 9

4-Amino-5-chloro-2-methoxy-N-[4-methyl-1-(1,4-diazacycloheptyl)]benzamide

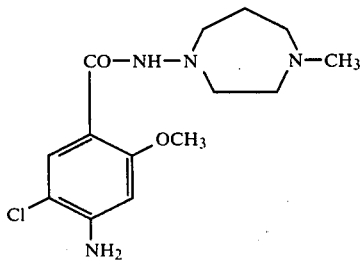

1-methylhomopiperazine (prepared as described by A. H. Sommers et al, in J. Amer. Chem. Soc. 76, 5805, 1954) (6.10 g, 0.0535 mole) was dissolved in concentrated hydrochloric acid (25 ml), cooled to 0°–5° C., stirred and treated dropwise with sodium nitrite (4.06 g) in water (10 ml). After addition the solution was allowed to come to room temperature, then heated for ½ hour at 70° C. The solution was cooled and basified with solid KOH and extracted with ether (3×100 ml). The dried ($K_2CO_3$) extracts yielded N-methyl-N'-nitrosohomopiperazine (3.80 g, 50%) as a pale yellow oil.

Lithium aluminium hydride reduction in anhydrous tetrahydrofuran as described in Example 5 gave N'-amino-N-methylhomopiperazine (1.8 g) as a colourless oil.

Subsequent reaction with 4-acetylamino-5-chloro-2-methoxy benzoic acid (3.5 g) and triethylamine (1.5 g) and hydrolysis as described in Example 1 gave 4-amino-5-chloro-2-methoxy-N-[4-methyl-1-(1,4-diazacycloheptyl)]benzamide (520 mg) as colourless microcrystals m.p. 141°–143° C. after purification by chromatography.

EXAMPLE 10

4-Amino-5-chloro-2-methoxy-N-{[4-(3-chlorobenzyl)]-1-piperazinyl}benzamide

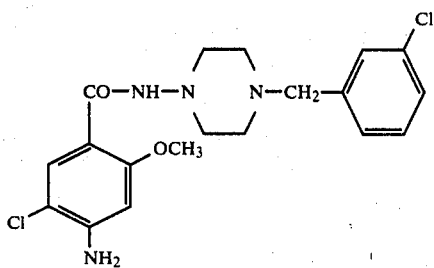

Reaction between 4-acetylamino-5-chloro-2-methoxybenzoic acid (3.75 g, 0.015 mole), triethylamine (3 ml) and N-amino-$N^1$-(3-chlorobenzyl)piperazine (3.61 g, 0.014 mole), followed by work up and hydrolysis as described in Example 1 gave 4-amino-5-chloro-2-methoxy-N{[4-(3-chlorobenzyl)]-1-piperazinyl}benzamide (2.49 g, 48%) as colourless microcrystals m.p. 211°–213° C. (ex EtOAc).

EXAMPLE 11

4-Amino-5-chloro-2-methoxy-N-[4-(2-thenyl)-1-piperazinyl]-benzamide

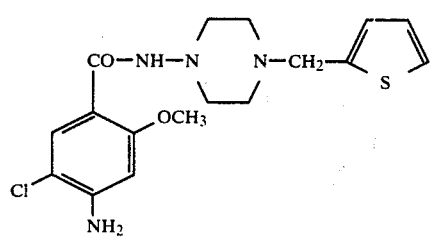

2-Chloromethylthiophene (prepared as described by F. F. Blicke and J. H. Burkhatter in J. Amer. Chem. Soc., 64, 477, 1947) (5.0 g, 0.038 mole) was added to acetone (100 ml) containing N-nitrosopiperazine (5.4 g, 0.038 mole) (prepared as described in U.S. Pat. No. 2,907,767), anhydrous potassium carbonate (6.0 g, 0.04 mole) and a catalytic amount of potassium iodide (1 small crystal). The mixture was heated under reflux for 3 hours, cooled, treated with water (50 ml) evaporated to ⅓ volume and extracted with ethylacetate (3×150 ml). The combined extracts were dried (anhydrous $K_2CO_3$), filtered and evaporated in vacuo to yield N-nitroso-N'-2-thenylpiperazine (7.35 g, >99%) as a straw coloured oil.

A solution of N-nitroso-N'-2-thenylpiperazine (3.0 g, 0.014 mole) in anhydrous freshly distilled tetrahydrofurane (30 ml) was added dropwise to a stirred suspension of lithium aluminium hydride (1.5 g excess) under nitrogen in anhydrous tetrahydrofuran (150 ml) at 60°–65° C. After addition, stirring was continued for 3 hours. Work-up via cooling, controlled addition of water (1.5 ml), 10% sodium hydroxide (2.25 ml) and water (3.75 ml) followed by filtration, drying over potassium carbonate, filtration and evaporation in vacuo gave N-amino-N'-2-thenyl-piperazine (2.7 g, 96%) as an almost colourless oil, used without further purification, 4-Acetylamino-5-chloro-2-methoxybenzoic acid (3.67 g, 0.015 mole) was treated with thionyl chloride (30 ml) at 50° for ½ hour. The mixture was evaporated in vacuo and the residue azeotroped twice with anhydrous toluene (100 ml), redissolved in hot anhydrous toluene (150 ml) and filtered. Triethylamine (2 ml) was added to the filtrate followed by N-amino-N'-2-thenylpiperazine (2.70 g, 0.0137 mole) and the reaction left for 6 hours at room temperature. The mixture was basified with 10% sodium hydroxide (10 ml) and the toluene layer separated, dried over $K_2CO_3$ and evaporated in vacuo to yield 4-acetylamino-5-chloro-2-methoxy-N-[1-(2-thenyl)-4-piperazinyl]-benzamide (3.7 g, 64%) as colourless microcrystals, m.p. 178°–181° C. (ex EtOAc-light petroleum 40°–60°).

Treatment of the above with 85% potassium hydroxide (700 mg) in aqueous ethanol (45 ml) for 6 hours at reflux gave on ethylacetate extraction, 4-amino-5-chloro-2-methoxy-N-[4-(2-thenyl)-1-piperazinyl]-benzamide (1.7 g, 70%), as colourless microcrystals, m.p. 225°–226° C. ex. EtOAc.

EXAMPLE 12

4-Amino-5-chloro-2-methoxy-N-[4-(3-thenyl)-1-piperazinyl]-benzamide

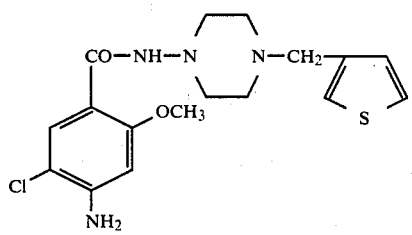

A suspension of 3-thenoic acid (prepared as described by S. Gronowitz in Arkiv. Kemi., 7, 361–369, 1954) (4.7 g, 0.037 mole) in anhydrous ether was treated with an ethereal solution of diazomethane (from 7-8 g N-nitroso-methylurea and 40% aqueous potassium hydroxide (30 ml) and ether (100 ml)). Evaporation in vacuo gave methyl-3-thenoate (4.9 g). Lithium aluminium hydride (1.3 g) reduction in ether gave 3-hydroxymethylthiophene (3.4 g, 93%) as a colourless oil.

Treatment of the above (3.0 g, 0.0263 mole) in anhydrous toluene with anhydrous hydrogen bromide for 5–10 minutes followed by addition of anhydrous magnesium sulphate filtration and evaporation in vacuo gave 3-bromomethylthiophene (2.93 g, 63%).

Alkylation of N-nitrosopiperazine (1.90 g, 0.0165 mole) with the above in a manner described in Example 11, gave N-3-thenyl-N'-nitroso-piperazine (3.48 g, >98%). Lithium aluminium hydride reduction in anhydrous tetrahydrofuran as described in Example 11, gave N-amino-N'-3-thenyl-piperazine (2.2 g, 69%).

Subsequent reaction with 4-acetylamino-5-chloro-2-methoxybenzoic acid (3.14 g) and triethylamine (1.5 g) followed by hydrolysis as described in Example 11 gave 4-amino-5-chloro-2-methoxy-N-[4-(3-thenyl)-1-piperazinyl]-benzamide (4.0 g, 85%) as off-white microcrystals, m.p. 223°–224° C. ex. chloroform-light petroleum 40°–60°.

EXAMPLES 13 to 16

The compounds shown in the table were prepared:

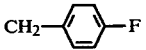

| Example No. | $R_7$ |
|---|---|
| 13 | n-$C_5H_{11}$ |
| 14 | $CH_2$-⌬-F |
| 15 | n-$C_3H_7$ |
| 16 | i-$C_3H_7$ | in the following manner:

Alkylation of N-nitrosopiperazine with the appropriate alkylating agent in a manner described in Example 11 furnished N-1-pentyl-; N-(4-fluorobenzyl)-; N-(1-propyl)-; and N-(2-propyl)-N'-nitrosopiperazines.

Lithium aluminium hydride reduction as described in Example 11 furnished the corresponding N'-aminopiperazines.

Subsequent reaction with 4-acetylaminobenzoic acid, and triethylamine followed by hydrolysis as described in Example 11 gave the following:

EXAMPLE 13

4-amino-5-chloro-2-methoxy-N-[4-(1-pentyl)-1-piperazinyl]-benzamide (41%), m.p. 137°–139° C.

EXAMPLE 14

4-amino-5-chloro-2-methoxy-N-[4-(4-fluorobenzyl)-1-piperazinyl]-benzamide (59%), m.p. 200°–205.5° C.

EXAMPLE 15

4-amino-5-chloro-2-methoxy-N-[4-(1-propyl)-1-piperazinyl]-benzamide (41%), m.p. 185.5°–187° C.

EXAMPLE 16

4-amino-5-chloro-2-methoxy-N-[4-(2-propyl)-1-piperazinyl]-benzamide (75%), m.p. 203.5°–204.5° C.

EXAMPLE 17 to 19

These examples illustrate the preparation of quaternary salts:

EXAMPLE 17

4-Amino-5-chloro-2-methoxy-N-[4-methyl-1-piperazinyl]-benzamide methobromide

4-Amino-5-chloro-2-methoxy-N-[1-methyl-4-piperazinyl]-benzamide (prepared as described in Example 2) (2.5 g, 0.0084 mole) was dissolved in acetone (50 ml) and treated with methyl bromide (ca. 2 g). The crystalline precipitate was filtered and recrystallised from ethanol (20 ml) to give 4-amino-5-chloro-2-methoxy-N-[4-methyl-1-piperazinyl]-benzamide methobromide (1.0 g, 30%) as colourless microcrystals m.p. 260.5° C.

EXAMPLE 18

4-Amino-5-chloro-2-methoxy-N-[4-methyl-1-piperazinyl]-benzamide benzobromide

4-Amino-5-chloro-2-methoxy-N-[1-methyl-4-piperazinyl]-benzamide (prepared as described in Example 2) (1.50 g, 0.005 mole) was dissolved in acetone (30 ml) and treated with benzylbromide (ca. 800 mg). The crystalline precipitate was filtered and recrystallised from ethanol/ethylacetate to give 4-amino-5-chloro-2-methoxy-N-[4-methyl-1-piperazinyl]-benzamide benzobromide (1.1 g, 47%) as colourless microcrystals m.p. 220° C.

EXAMPLE 19

4-Amino-5-chloro-2-methoxy-N-[4-n-butyl-1-piperazinyl]-benzamide methobromide

4-Amino-5-chloro-2-methoxy-N-[1-n-butyl-4-piperazinyl]-benzamide (prepared as described in Example 6) (1.50 g, 0.0044 mole) was dissolved in acetone (30 ml) and treated with methyl bromide (ca. 2 g) portionwise. Filtration and retreatment of mother liquors with methyl bromide gave successive crops of crystalline material, m.p. 257°–260° C. Recrystallisation from ethanol/EtOAc gave 4-amino-5-chloro-2-methoxy-N-[4-n-butyl-1-piperazinyl]-benzamide methobromide (1.75 g, 91%) as colourless microcrystals m.p. 259°–260° C.

EXAMPLE 20

4-Amino-5-chloro-2-methoxy-N-[4-(3-methylbutyl)-1-piperazinyl]-benzamide

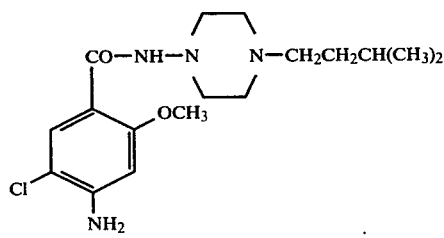

A mixture of 3-methyl-1-bromo-butane (3.94 g.), N-nitroso-piperazine (3 g.), anhydrous potassium carbonate (3.6 g.) and a small crystal of potassium iodide in dimethyl formamide was heated at 100° for 2 hours. Solvent was removed under reduced pressure and the residue dissolved in ether and water. The ether extract was separated, dried and evaporated to give an oil which was adsorbed on silica gel. Elution with ethyl acetate gave N-(3-methylbutyl)-N'-nitroso piperazine, further purified by dissolving in dilute acid, washing the acid extract with ether, basifying the acid extract and re-extracting with ether. The yield of colourless oil was 3 g (62%).

A solution of N-(3-methyl-butyl)-N'-nitrosopiperazine (3 g.) in anhydrous tetrahydrofuran (30 ml). was added dropwise to a stirred suspension of lithium aluminium hydride (0.65 g.) in anhydrous tetrahydrofuran (100 ml.) under nitrogen at 50°. After 30 minutes, the mixture was cooled and worked up in the usual manner to give crude N-(3-methylbutyl)-N'-amino-piperazine (2.5 g.) used without purification in the next step.

N-(3-methyl-butyl)-N'-nitroso-piperazine (2.5 g.) was added to 4-acetylamino-5-chloro-2-methoxy-benzoyl chloride (prepared from 3.5 g. of corresponding acid and thionylchloride) and triethylamine (5 ml.) in anhydrous toluene (250 ml.). After 1 hour, 10% sodium hydroxide (5 ml.) was added and the toluene layer separated, dried and evaporated to give 4-acetylamino-5-chloro-2-methoxy-N-[4-(3-methylbutyl)-1-piperazinyl]-benzamide (3 g., 52%), m.p. 128°-30° (ex-ethylacetate/-light petroleum.

Treatment of the 4-acetylamino compound (3 g.) with potassium hydroxide (1.2 g) in 95% ethanol (20 ml.) for 4 hours at reflux gave, after evaporation and extraction of the residue with ethyl acetate, 4-amino-5-chloro-2-methoxy-N-[4-(3-methylbutyl)-1-piperazinyl]-benzamide (1.66 g., 62%), m.p. 174°-6° (ex-ethyl acetate/light petroleum.

EXAMPLE 21

4-Amino-5-bromo-2-methoxy-N-[4-methyl-1-piperazinyl]-benzamide hemihydrate

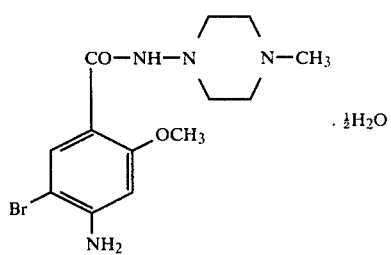

Reaction between 4-acetylamino-5-bromo-2-methoxybenzoyl chloride (prepared from 2.1 g. of corresponding acid and thionyl chloride), N-amino-N'-methyl piperazine (0.85 g.) and triethylamine (2 ml.) in toluene followed by alkaline hydrolysis as described in Example 20 gave 4-amino-5-bromo-2-methoxy-N-[4-methyl-1-piperazinyl]-benzamide hemihydrate (1.78 g., 68%) m.p. 174°-6° (ex-chloroform).

EXAMPLE 22

4-Amino-5-chloro-2-methoxy-N-[4-n-butyl-1-(1-4-diazocycloheptyl)]benzamide

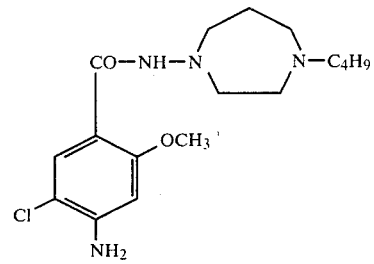

1-n-butylpiperidone (prepared as described by N. Barbulescu et al, in Rev. Chim. (Bucharest) 1969, 20 (4), 193–5, C.A. 71 38844 g) (15.5 g, 0.1 mole) was dissolved in chloroform (100 ml), treated cautiously with concentrated sulphuric acid (90 ml) and the mixture cooled to 10° C. Sodium azide (7.1 g, 0.11 mole) was added portionwise over ½ hour. The mixture was stirred for a further ½ hour and the chloroform separated. Evaporation in vacuo gave 1-n-butyl-5-oxo-1-4 diazacycloheptane (15.42 g 79%). Lithium aluminium reduction in ahydrous tetrahydrofuran under nitrogen atmosphere gave 1-n-butyl-1-4-diazacycloheptane (70%) Subsequent nitrosation, lithium aluminium hydride reduction and reaction with 4-acetylamino-5-chloro-2-methoxy benzoic acid as described in Example 9 gave 4-amino-5-chloro-2-methoxy N-[4-n-butyl-1-(1-4-diazacycloheptyl)]benzamide (85%) as colourless microcrystals mp 126°–127°.

EXAMPLE 23

4-Amino-5-chloro-2-methoxy-N-[4-(4-dimethylaminobenzyl)-1-piperazinyl]benzamide

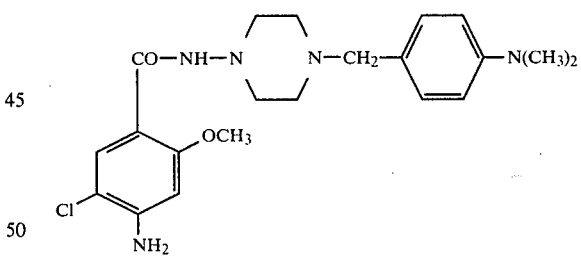

4-Dimethylaminobenzoic acid (10.0 g, 0.06 mole) was treated with thionyl chloride (30 ml) at 50° C. for 20 minutes. The resulting solution was evaporated in vacuo and the residue azeotroped twice with toluene. The resulting acid chloride in toluene was treated with triethylamine (6.1 g) then N-nitrosopiperazine (7.0 g). Work up as described in Example 1 gave N-4-dimethylaminobenzoyl-N'-nitrosopiperazine (15.0 g 95%). Hydrogenation at 50 psi in ethanol in the presence of Raney Nickel for 12 hours gave N-4-dimethylaminobenzoylpiperazine (99%). Lithium aluminium hydride reduction in anhydrous tetrahydrofuran at 50° C. gave N-4-dimethylaminobenzylpiperazine (60%).

Subsequent nitrosation, lithium aluminium hydride reduction and treatment with 4-acetylamino-5-chloro-2-methoxybenzoic acid as described in Example 9 gave 4-amino-5-chloro-2-methoxy N-[4-(4-dimethylaminobenzyl)-1-piperazinyl]benzamide (52%) as light brown microcrystals mp 208°-210° C.

PHARMACOLOGICAL DATA

1. Compounds prepared in the Examples were tested for the following pharmacological activities in the rat:
  (a) Increase in intragastric pressure Intragastric pressure changes were recorded from previously starved conscious but restrained rats using a saline filled catheter inserted into the lumen of the stomach via a permanent gastric fistula. The catheter was connected to a physiological pressure transducer and pressure changes recorded on a hot wire pen recorder. In each animal a pre dose period of 40 minutes was allowed to obtain a measure of spontaneous activity. An index of activity was obtained by measuring the average height of pressure waves during 10 minute periods. Values for 4 such periods were obtained during assessment of spontaneous activity and for the 40 minute period after the subcutaneous administration of the Compounds. Student "t" test was applied to the difference in average values obtained for spontaneous and post Compound activity.

(b) Increase in gastric emptying-reversal of apomorphine induced delay in gastric emptying of a test meal.

Rats equipped with chronic gastric fistual were used and it was through this that 5 ml of a test meal (5 ml phosphate buffer at pH 9) was administered and recovered. The % recovery of the standard meal after remaining in the stomach for 10 minutes was taken as an index of gastric emptying. Delay in gastric emptying was induced by the administration of Apomorphine HCl (5 mg/kg subcutaneously) and was given 15 minutes prior to the subcutaneous administration of the Compound. The % recoveries of the test meal was determined at 15-25 and 45-55 minutes post dosing with the Compound and compared with vehicle only dosed animals set up simultaneously. Six animals were used for each group.

(c) Inhibition of stereotype behaviour induced by apomorphine

This is indicative of dopamine receptor blockade in the central nervous system.

The method of Ernst A.M. (1967) Pyschopharmocologia (Berl.) 10 pp. 316-323 was followed.

Table 1 shows active doses (mg/kg) in these tests either by the subcutaneous (s.c.) or oral (p.o.) route of administration.

TABLE 1

| Example No. | (a) Increase in Intra-gastric Pressure | (b) Increase in Gastric Emptying | (c) Inhibition of Stereotype Behaviour |
|---|---|---|---|
| 1 |  | 25 mg s.c. | 0.625 mg s.c. |
| 2 | 1 mg s.c. 20 mg p.o. | 25 mg s.c. | Inactive (100 mg s.c.) |
| 4 | 10 mg p.o. |  |  |
| 5 | 50 mg s.c. | 50 mg s.c. | Inactive (50 mg s.c.) |
| 6 | 5 mg s.c. | 25 mg s.c. | Inactive (25 mg s.c.) |
| 7 |  |  | 50 mg s.c. |
| 8 |  | 25 mg s.c. | 3 mg s.c. |
| 9 | 10 mg s.c. | 25 mg s.c. | Inactive (25 mg s.c.) |
| 11 | 50 mg s.c. (slightly active) |  | Inactive (50 mg s.c.) |
| 12 |  | 50 mg s.c. | 50 mg s.c. |
| 13 |  |  | 50 mg s.c. |
| 14 |  | 50 mg s.c. | 50 mg s.c. |
| 15 | 10 mg s.c. | 50 mg s.c. (slightly active) | Inactive (50 mg s.c.) |
| 16 | 5 mg s.c. |  | Inactive (50 mg s.c.) |
| 17 | 0.5 mg s.c. |  | Inactive (50 mg s.c.) |
| 18 | 25 mg s.c. | 25 mg S.C. | Inactive (50 mg s.c.) |
| 19 | 1 mg s.c. | 50 mg s.c. (slightly active) | Inactive (50 mg s.c.) |
| 20 |  |  | Slightly active (50 mg s.c.) |
| 21 | 5 mg s.c. | 50 mg s.c. | Inactive (50 mg s.c.) |

2. Anti- emetic activity in the dog
  (a) Compounds were tested in the dog for their ability to abolish the emetic response to apomorphine. The results are shown in Table 2.

TABLE 2

| Example No. | $ED_{50}$ |
|---|---|
| 1 | .0125 mg/kg s.c. |
| 2 | 8 mg/kg s.c. |
| 6 | 1 mg/kg s.c. |
| 9 | slight activity at 2 mg/kg s.c. (inhibition of no. of vomits only) |
| 13 | 0.36 mg/kg s.c. |
| 20 | 0.35 mg/kg s.c. |

(b) At 5 mg/kg subcutaneously, the compound of Example 22 completely inhibited apomorphine induced emesis in the dog.

3. The compound of Example 23 was shown to have potential neuroleptic activity in two tests:
  (i) At a dose level of 10 mg/kg subcutaneously this compound inhibited by 25% amphetamine induced stereotypy in rats.
  (ii) The compound also inhibited catapresan induced fighting behaviour in mice; the $ED_{50}$ value for such activity being 60 mg/kg orally.

The methodology for tests (i) and (ii) was as follows:

Antagonism of Amphetamine Stereotypy

Based on method of Jansen, Niemegeers and Schellekens (1966), Arzneimittel Forsch., 15, pp. 104-117. Rats were given compound 15 minutes prior to subcutaneous injection of d-amphetamine (10 mg/kg). 30 minutes and 1 hour after the amphetamine, the degree of stereotyped behaviour was scored according to the method of Costal, Naylor and Olley (1972). Europ. J. Pharmacol., 18, pp. 83-94. The percentage inhibition of stereotypy at the respective time interval was calculated.

Catapresan Test

Catapresan (20-25 mg/kg intravenously) was used to induce fighting behaviour in mice. The fighting was assessed as the biting of a dead mouse placed in the cage and was given a score of 1 or 2 depending on intensity.

Compound effect was measured as percentage inhibition of fighting compared to that with control animals and the dose reducing fighting by 50% was determined graphically.

4. Toxicity

None of the compounds tested showed any signs of toxicity at the active doses.

I claim:

1. A compound of the formula:

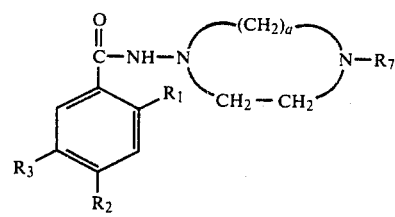

and the pharmaceutically acceptable acid addition and quaternary salts thereof, wherein $R_1$ is alkoxy of 1 to 6 carbon atoms;

$R_2$ is —$NH_2$ or alkanoylamino of 2 to 7 carbon atoms;

$R_3$ is hydrogen or halo;

$R_7$ is alkyl of 1 to 6 carbon atoms unsubstituted or monosubstituted with phenyl, said phenyl being unsubstituted or monosubstituted by halo, alkyl of 1 to 6 carbon atoms, alkoxy of 1 to 6 carbon atoms, hydroxy, nitro, trifluoromethyl, amino, or mono- or dialkylamino wherein alkyl contains from 1 to 6 carbon atoms; and a has a value of 2 or 3.

2. The compound according to claim 1 wherein $R_7$ is benzyl, chlorobenzyl, methoxybenzyl or alkyl of 1 to 6 carbon atoms.

3. A compound as claimed in claim 1 wherein $R_2$ is amino.

4. A compound as claimed in claim 3 wherein $R_3$ is chloro.

5. A compound as claimed in claim 4 wherein $R_1$ is methoxy.

6. A compound according to claim 1 wherein $R_2$ is alkanoylamino.

7. A compound according to claim 6 wherein $R_2$ is acetylamino.

8. A compound according to claim 1 wherein a has a value of 2.

9. A compound according to claim 1 wherein $R_7$ is alkyl of 1 to 6 carbon atoms.

10. A compound according to claim 1 wherein $R_7$ is phenyl-alkyl wherein alkyl has 1 to 3 carbons.

11. A compound according to claim 1 wherein $R_1$ is methoxy, $R_2$ is amino, $R_3$ is chloro and a is 2.

12. A compound as claimed in claim 11 wherein $R_7$ is phenylalkyl.

13. A compound according to claim 12 wherein $R_7$ is benzyl.

14. A compound according to claim 11 wherein $R_7$ is alkyl of 1 to 6 carbon atoms.

15. A compound according to claim 14 wherein $R_7$ is methyl.

16. A compound according to claim 14 wherein $R_7$ is n-butyl.

17. A compound according to claim 1 which is the hydrochloride, hydrobromide, phosphate, sulfate, citrate, tartarate, lactate or acetate salt of said benzamide.

18. A compound according to claim 1 which is 4-amino-5-chloro-2-methoxy-N-(4-benzyl-1-piperazinyl)-benzamide.

19. A compound according to claim 1 which is 4-acetylamino-5-chloro-2-methoxy-N-(4-benzyl-1-piperazinyl)-benzamide.

20. A compound according to claim 1 which is 4-amino-5-chloro-2-methoxy-N-(4-methyl-1-piperazinyl)-benzamide.

21. A compound according to claim 1 which is 4-acetylamino-5-chloro-2-methoxy-N-(4-methyl-1-piperazinyl)benzamide.

22. A compound according to claim 1 which is 4-amino-5-chloro-2-methoxy-N-(4-ethyl-1-piperazinyl)-benzamide.

23. A compound according to claim 1 which is 4-acetylamino-5-chloro-2-methoxy-N-(4-ethyl-1-piperazinyl)benzamide.

24. A compound according to claim 1 which is 4-amino-5-chloro-2-methoxy-N-(4-n-butyl-1-piperazinyl)-benzamide.

25. A compound according to claim 1 wherein $R_7$ is alkyl of 1 to 6 carbon atoms, or phenylalkyl wherein alkyl has 1 to 6 carbon atoms and said phenyl is unsubstituted or substituted by halo, or alkoxy of 1 to 6 carbon atoms.

26. A compound according to claim 1 wherein $R_3$ is bromo.

27. A compound according to claim 11 wherein $R_7$ is thienylalkyl wherein the alkyl contains 1 to 3 carbon atoms.

28. A compound according to claim 11 which is the hydrochloride, hydrobromide, phosphate, sulphate, citrate, tartarate, lactate or acetate salt of said benzamide.

29. A compound according to claim 11 which is a quaternary ammonium salt of said benzamide.

30. The hydrochloride salt of a compound according to claim 11.

31. A pharmaceutical composition comprising a pharmacologically effective amount of a compound according to claim 1 in combination with a pharmaceutically acceptable carrier.

32. A method of regulating gastrointestinal function and effecting an antimetic response in an animal which comprises administration of a compound according to claim 1.

33. A compound according to claim 1 which is 4-amino-5-chloro-2-methoxy-N-[4-(4-chlorobenzyl)-1-piperazinyl]-benzamide.

34. A compound according to claim 1 which is 4-amino-5-chloro-2-methoxy-N-[4-(4-methoxybenzyl)-1-piperazinyl]-benzamide.

35. A compound according to claim 1 which is 4-amino-5-chloro-2-methoxy-N-[4-methyl-1-(1,4-diazacycloheptyl)]-benzamide.

36. A compound according to claim 1 which is 4-chloroacetylamino-5chloro-2-methoxy-N-[4-methyl-1-piperazinyl]-benzamide.

37. A compound according to claim 1 which is 4-amino-5-chloro-2-methoxy-N-[4-(3-chlorobenzyl)-1-piperazinyl]-benzamide.

* * * * *